(12) United States Patent
Saggiomo et al.

(10) Patent No.: US 11,052,388 B2
(45) Date of Patent: Jul. 6, 2021

(54) METHOD OF MANUFACTURING A MICROFLUIDIC DEVICE

(71) Applicant: Wageningen Universiteit, Wageningen (NL)

(72) Inventors: Vittorio Saggiomo, Wageningen (NL); Aldo Hendrikus Velders, Zutphen (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 191 days.

(21) Appl. No.: 15/561,905

(22) PCT Filed: Mar. 27, 2015

(86) PCT No.: PCT/EP2015/056728
§ 371 (c)(1),
(2) Date: Sep. 26, 2017

(87) PCT Pub. No.: WO2016/155760
PCT Pub. Date: Oct. 6, 2016

(65) Prior Publication Data
US 2018/0126375 A1    May 10, 2018

(51) Int. Cl.
*B01L 3/00* (2006.01)
*B29C 33/38* (2006.01)
(Continued)

(52) U.S. Cl.
CPC .... *B01L 3/502707* (2013.01); *B29C 33/3842* (2013.01); *B29C 33/52* (2013.01);
(Continued)

(58) Field of Classification Search
CPC ....... B01L 3/502707; B01L 2300/0874; B81C 1/00119; B81C 2201/0108; B29C 33/52;
(Continued)

(56) References Cited

U.S. PATENT DOCUMENTS 9,574,172 B2 *   2/2017   Lenardi .................. B29C 45/00
9,815,054 B2 *  11/2017   Tofteberg .......... B29C 45/14065
(Continued)

FOREIGN PATENT DOCUMENTS

DE        102004011667 A1 *  11/2005   ........ B01L 3/502707
EP        2 826 814 A1       1/2015
(Continued)

OTHER PUBLICATIONS

Machine translation for DE 102004011667B4 (Year: 2006).*
International Search Report and Written Opinion in PCT/EP2015/056728 dated Nov. 24, 2015, 10 pgs.

*Primary Examiner* — Timothy Kennedy
*Assistant Examiner* — Alexander A Wang
(74) *Attorney, Agent, or Firm* — Squire Patton Boggs (US) LLP

(57) ABSTRACT

A method of manufacturing a microfluidic device, said method comprising placing a length of material in a liquid polymer, configuring the length of material to define the path of a microfluidic channel, curing or setting the polymer liquid to form a solid polymer around the configured length of material, and dissolving the configured length of material with a solvent to provide a microfluidic channel in the solid polymer.

14 Claims, 3 Drawing Sheets

(51) Int. Cl.
- B29C 33/52 (2006.01)
- B81C 1/00 (2006.01)
- B29L 31/00 (2006.01)
- B29K 83/00 (2006.01)
- B33Y 80/00 (2015.01)

(52) U.S. Cl.
CPC ... B81C 1/00119 (2013.01); *B01L 2300/0874* (2013.01); *B29K 2083/00* (2013.01); *B29K 2855/02* (2013.01); *B29L 2031/756* (2013.01); *B33Y 80/00* (2014.12); *B81C 2201/0108* (2013.01)

(58) Field of Classification Search
CPC ........ B29C 33/3842; B29C 2201/0108; B29C 1/00119; B33Y 80/00; B29K 2855/02; B29K 2083/00; B29L 2031/756
See application file for complete search history.

(56) References Cited

U.S. PATENT DOCUMENTS

| | | |
|---|---|---|
| 2002/0092962 A1 | 7/2002 | Domeier et al. |
| 2003/0087198 A1 | 5/2003 | Dharmatilleke et al. |
| 2003/0214057 A1 | 11/2003 | Huang |
| 2006/0201883 A1* | 9/2006 | Hofmeister ........ B01D 39/1676 210/649 |
| 2007/0012891 A1 | 1/2007 | Maltezos et al. |
| 2015/0035200 A1 | 2/2015 | Karpas et al. |

FOREIGN PATENT DOCUMENTS

| | | |
|---|---|---|
| WO | WO 2005/088710 A1 | 9/2005 |
| WO | WO 2007/021762 A2 | 2/2007 |
| WO | WO 2012/164512 A1 | 12/2012 |
| WO | WO 2014/178726 A1 | 11/2014 |

\* cited by examiner

METHOD OF MANUFACTURING A MICROFLUIDIC DEVICE

CROSS-REFERENCE TO RELATED APPLICATIONS

This application is a National Stage filing under 35 USC § 371 of International Patent Application No. PCT/EP2015/056728, filed Mar. 27, 2015, entitled "A METHOD OF MANUFACTURING A MICROFLUIDIC DEVICE," which is incorporated herein by reference in its entirety for all purposes.

Microfluidic devices are currently used in many different fields, stretching from chemistry and biology to physics and engineering. These devices include microfluidic channels for transporting fluids from one part of the device to another. The fluids may be mixed and/or analysed on the device. Accordingly, microfluidic devices have extensive applications as lab-on-chip devices.

Polydimethylsiloxane (PDMS) is commonly used for the fabrication of microfluidic devices. It is relatively inexpensive, gas permeable and has a refractive index of 1.4, close to that of glass.

Various methods for fabricating microfluidic devices are known. In one such method, a silicon master is generated by photolithography. Here, light is used to transfer a geometric pattern from a photomask to a light-sensitive layer or photoresist deposited on a silicon substrate. A master pattern is then engraved according to the geometric pattern into the photoresist. The engraved pattern shows the microfluidic channels in positive relief. A material, such as liquid PDMS pre-polymer, is then poured over the master and cured, so that the microfluidic channels are moulded into PDMS in negative relief. The PDMS replica is then peeled from the master and the replica is sealed to a flat surface to enclose the microfluidic channels.

Although the process is effective, it is highly time-consuming and requires a high level of skill. Furthermore, the fabrication of 3-D channels is difficult as multiple layers of 2-D channels are required to be stacked together.

According to the present invention, there is provided a method of manufacturing a microfluidic device, said method comprising placing a length of material in a liquid polymer,
configuring the length of material to define the path of a microfluidic channel,
curing or setting the polymer liquid to form a solid polymer around the configured length of material, and
dissolving the configured length of material with a solvent to provide a microfluidic channel in the solid polymer.

For the avoidance of doubt, the length of material may be configured before or after placing the length of material in a liquid polymer. However, the length of material is preferably configured prior to being placed in the liquid polymer. The length of material may be configured into the desired configuration by any suitable method, including moulding and 3-D printing. Alternatively, the material may be bent into shape, for example, using heat. The material may be relatively inflexible at room temperature but may become malleable at higher temperatures. For example, the material may be shaped into various forms at elevated temperatures, for example, of 70° C. or more.

The present inventors have found that it is possible to configure and set a length of material in the polymer as a scaffold, which is subsequently dissolved using a solvent to leave a microfluidic channel within the polymer. This allows a microfluidic channel to be produced either in two or three dimensions in a convenient and effective manner.

Preferably, at least a portion of the configured length of material protrudes from the solid polymer. More preferably, the ends of the configured length of material protrude from the solid polymer. The exposed portions of material are more readily accessible by solvent, allowing the dissolution of the material to be initiated more readily.

Any suitable polymer may be used as the liquid polymer that is set around the configured length of material. Preferably, the liquid polymer is polydimethylsiloxane (PDMS). Other examples include epoxy-based polymers (e.g. SU-8); polyacrylamides and agarose gel. The polymers may be cured using a curing agent on exposure to, for example, heat or light (e.g. UV radiation). The length of material is desirably insoluble in the liquid polymer. Moreover, if the liquid polymer is cured by, for example, exposure to elevated temperatures, the temperatures required for curing is desirably sufficiently low to avoid causing the length of material to lose its configured shape. Any suitable material may be used as the length of material. In a preferred embodiment, the length of material is a length of polymer filament. Suitable polymers may be selected from acrylonitrile butadiene styrene, polylactic acid, polystyrene (preferably high impact polystyrene) and polyvinyl acetate. Preferably, the length of material is a length of acrylonitrile butadiene styrene.

Any suitable solvent may be used to dissolve the configured length of material. The precise nature of the solvent will depend on the nature of the material used. For example, where the length of material is acrylonitrile butadiene styrene, acetone may be employed as the solvent. Where the length of material is formed of polylactic acid or polyvinyl acetate, an alkali solution (e.g. an aqueous hydroxide, such as aqueous sodium hydroxide) may be used as a solvent. Where high impact polystyrene is used as the length of material, D-limonene may be used as the solvent. When acetone is used as solvent, dichloromethane may be added to aid the removal of the length of material.

Preferably, mechanical and/or electronic components may be suspended and set in the polymer. Examples of such components include valves, mixing vessels, LEDs, heating elements, conductive wires, magnets and sensors. Such components may be embedded in the polymer, for example, adjacent or in communication with the microfluidic channel(s). In one embodiment, a component may be included in a channel by first forming or moulding the length of material (e.g. acrylonitrile butadiene styrene) around the component. The length of material containing the component is then suspended in the liquid polymer (e.g. PDMS), which is subsequently cured or set. When the length of material is dissolved using a solvent, the component is left in the desired position within the microfluidic channel. The solvent (e.g. acetone) used to dissolve the length of material is advantageously selected so as to be non-corrosive to the component.

In another embodiment, it is possible to position a component adjacent a microfluidic channel. For example, a length of metal coil may be wrapped around the length of material (e.g. acrylonitrile butadiene styrene) configured to define the path of the microfluidic channel. The wrapped material may then be suspended in the liquid polymer (e.g. PDMS), which is subsequently cured or set. When the length of material is dissolved using a solvent, the metal coil is positioned around the microfluidic channel. By ensuring that the ends of the length of metal protrude from the set polymer (e.g. PDMS), it is possible to e.g. pass a current through the metal wire, for example, to heat in that region of the microfluidic device.

These and other aspects of the present invention will now be described, by way of example, with reference to the accompanying drawings in which.

EXAMPLE 1

SYLGARD silicone elastomer 184 and SYLGARD silicone elastomer 184 curing agent were obtained from Dow Corning Corporation. A 3D SIMO pen was used for extruding 1.7 mm acrylonitrile butadiene styrene (ABS), plastic filament that was obtained from the same vendor. 3D print of Hilbert cube was ordered online and 3D printed by ridix.nl (Rotterdam, the Netherlands) using a Dimension SST 1200es printer and by 3dhubs.com using a Duplicator 4 printer. Acetone was obtained from Sigma Aldrich.

Figure 1:
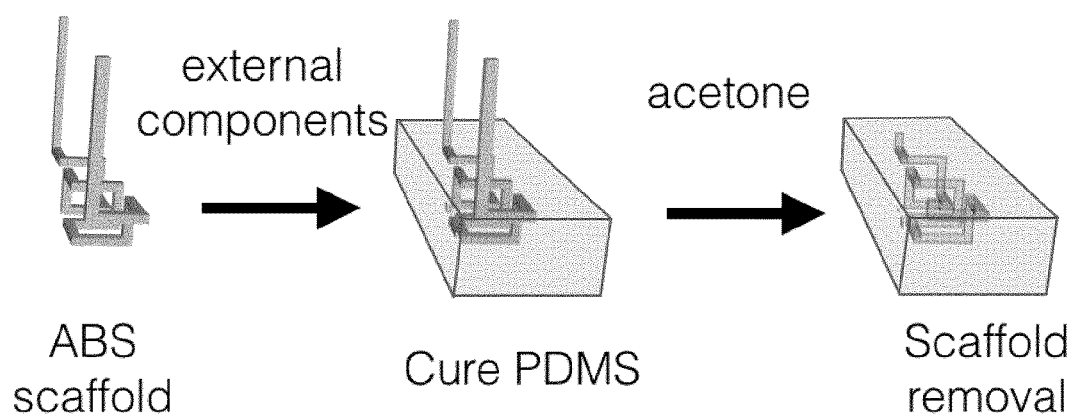
FIG. 1 is a schematic diagram showing the steps required to perform a method according to Example 1 of the present invention.

The ABS plastic filament was extruded through a 500 µm nozzle (3D SIMO pen) and then modeled into the desired 3D shape with the help of a soldering iron set (100° C.) or printed with a fused deposition modeling 3D printer (see FIG. 1). The modeled ABS plastic scaffold was then immersed in a well mixed solution of 10:1 sylgard 184/sylgard 184 curing agent. The PDMS was then placed under vacuum for removing air bubbles and cured for 2 hours at 75° C., or overnight at room temperature. The PDMS was consecutively left for 12 hours in acetone, after which the microchannels were cleaned with acetone and dried with a flow of compressed air.

EXAMPLE 2

Figure 2:
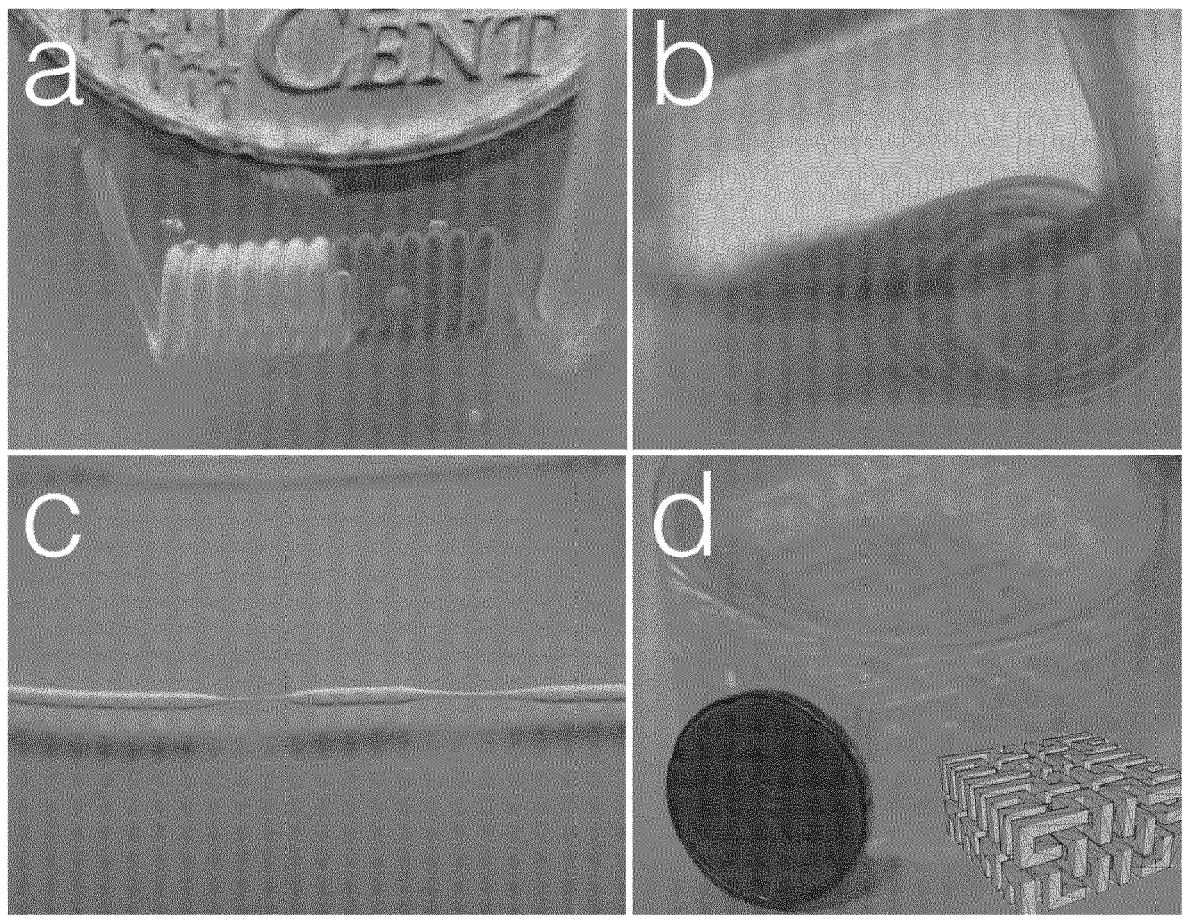
FIGS. 2a to 2d depict examples of microfluidic channels formed according to Example 2 of the present invention.

Using a similar procedure to that described with reference to Example 1, many different 3D channels were readily created. These are depicted in FIGS. 2a to 2d. FIG. 2a shows spiral channels. FIG. 2b shows multiple microfluidic channels with different geometries. FIG. 2c shows microfluidic channels with compartments differing in size. FIG. 2d shows a complex 3D multilevel scaffold based on the Hilbert curve. The ABS polymer scaffold was 3D-printed utilizing ABS fuse deposition modeling. The microfluidic channel depicted in FIG. 2d was formed from a scaffold that was 35 cm long and formed of 1.4 mL of ABS. Nonetheless, it was still possible to remove the plastic with subsequent baths in dichloromethane and acetone.

EXAMPLE 3

In this example, electronic circuitry, heating elements and RF components were incorporated in the microfluidic device.

Figure 3:
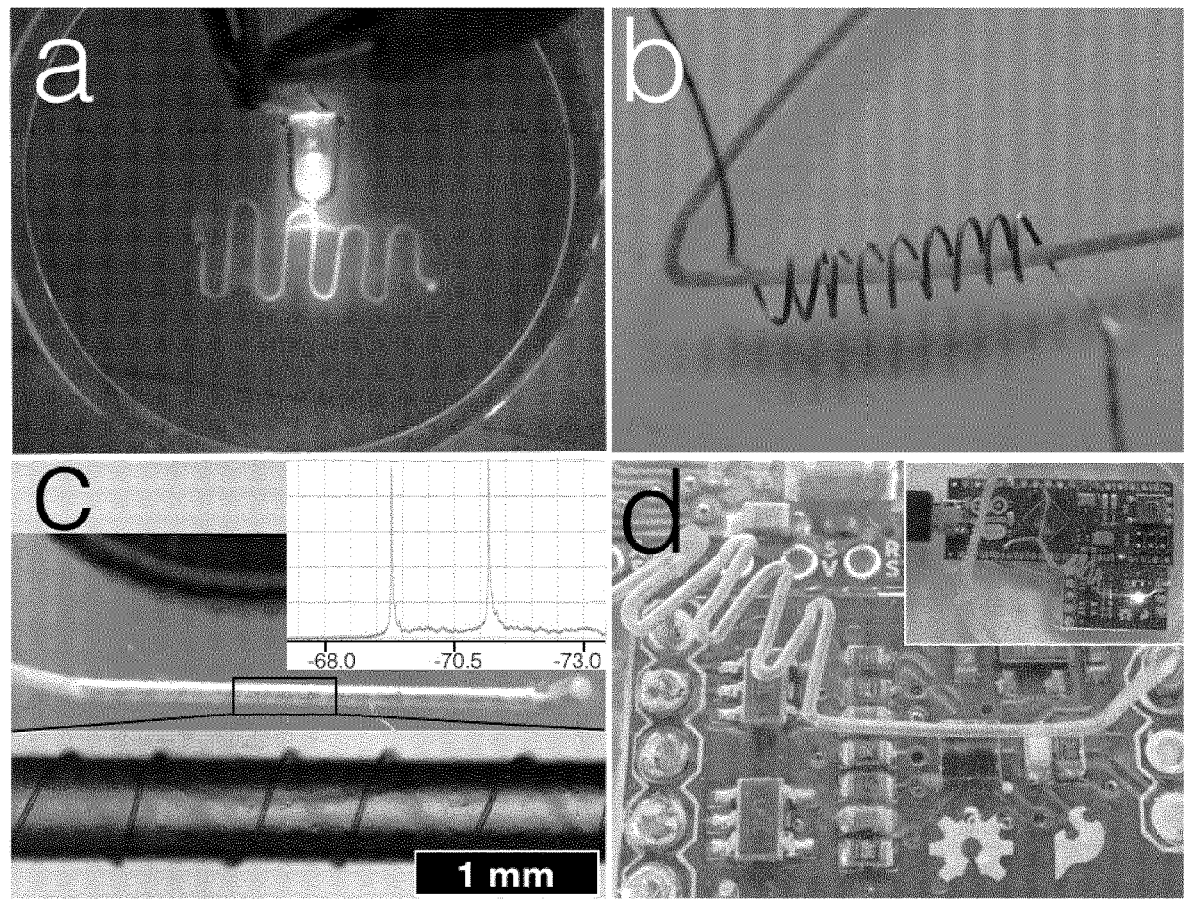
FIGS. 3a to 3d depict examples of electronic components incorporated into devices formed according to Example 3 of the present invention.

FIG. 3a depicts a microfluidic device containing an embedded 390 nm LED, for example, for optical detection or electronic excitation of chemicals in the microfluidic channel. The LED was inserted in the PDMS together with the scaffold before curing. Then, acetone treatment was used to remove only the scaffold, leaving the electronics intact.

FIG. 3b depicts a microfluidic device containing a selective heating unit. A 200 µm nichrome resistance wire was loosely wrapped around the ABS polymer scaffold and inserted in PDMS. After curing and dissolving the ABS scaffold, a voltage of 1.2 V and current of 0.35 A was applied to the wire. This sufficed for selectively heating a thermochromic dye above 27° C. only in the part of the channel surrounded by the resistance wire. Temperatures can be varied and the 200 µm wire can be used, for example, to boil water inside the channel. This simple and selective heating element embedded in the microfluidic chip can be of great value for designing chips to perform, e.g., biological experiments like PCR, sterilization inside the microchannels or for setting different temperatures for organ-on-chips or cell cultures.

FIG. 3c depicts a microfluidic device containing a solenoidal NMR microcoil. A 32 µm copper wire was wrapped around a 500 µm ABS filament, resulting in a final channel encompassed by a solenoidal NMR microcoil (FIG. 3c), with a detection volume of only 2 µL (normal NMR tubes contain about 500 µL sample volume). Because the transceiver coil matched the size of the sample, the sensitivity of the system was good. This microfluidic device was integrated on a cylindrical aluminum probe insert and placed inside a 9.4 Tesla narrow-bore superconducting NMR magnet. Tuning the resonance circuit to 376 MHz allowed high-resolution NMR spectra to be obtained (see FIG. 3c insert for spectrum). Line-widths at half peak-height were obtained of about 3 Hz and resolving heteronuclear spin-spin couplings, opening up the way to further optimization and applications. In addition, it was calculated that the material costs for fabricating this device is less than 2 Euro.

FIG. 3d depicts a microfluidic device comprising an embedded color sensor and a microcontroller. An Arduino micro and a color sensor were wired together and immersed in PDMS with an ABS scaffold. After curing the PDMS and removing the ABS polymer with acetone, the resulting microfluidic channel was right on top of the color sensor. Hooking up the Arduino to a computer revealed all the components of the microcontroller and the sensor to be working properly.

The invention claimed is:

1. A method of manufacturing a microfluidic device, said method comprising
   a. placing together in a liquid polymer,
      (a) a length of material that is configured to define the path of a microfluidic channel, and
      (b) at least one prefabricated mechanical or prefabricated electronic component, or a combination thereof where said length of material and said prefabricated mechanical and/or prefabricated electronic component(s) are together suspended in the liquid polymer,
   b. curing or setting the polymer liquid to form a solid polymer around the configured length of material and the prefabricated mechanical and/or prefabricated electronic component(s), and
   c. dissolving the configured length of material with a solvent to provide a microfluidic channel in the solid polymer comprising said prefabricated mechanical and/or prefabricated electronic component(s); wherein the length of material is formed around the prefabricated mechanical and/or prefabricated electronic component(s) and together suspended in the liquid polymer or wherein the prefabricated mechanical and/or prefabricated electronic component(s) is/are wrapped around the length of material and together suspended in the liquid polymer.

2. The method as claimed in claim 1, wherein the length of material is configured before placing the length of material in a liquid polymer.

3. The method as claimed in claim 1, wherein at least a portion of the configured length of material protrudes from the solid polymer.

4. The method as claimed in claim 3, wherein the ends of the configured length of material protrude from the solid polymer.

5. The method as claimed in claim 1, wherein the length of material is a length of polymer filament formed from a polymer selected from acrylonitrile butadiene styrene, polylactic acid, polystyrene and polyvinyl acetate.

6. The method as claimed in claim 5, wherein the length of material is a length of acrylonitrile butadiene styrene.

7. The method as claimed in claim 6, wherein the solvent is acetone.

8. The method as claimed in claim 7, wherein dichloromethane is employed as a co-solvent.

9. The method as claimed in claim 1, wherein the liquid polymer is a silicone elastomer and a curing agent.

10. The method of claim 9, wherein the silicone elastomer is Polydimethylsiloxane.

11. The method as claimed in claim 1, wherein radio frequency (RF) and/or prefabricated electronic components are suspended in the liquid polymer and set in the polymer when it is cured or set.

12. The method as claimed in claim 1, wherein the length of material is configured to define the configuration of the microfluidic channel by 3D-printing or modeling the length of material.

13. The method as claimed in claim 1, wherein the microfluidic channel is configured in three dimensions.

14. The method as claimed in claim 1, wherein the prefabricated mechanical and/or prefabricated electrical component(s) is/are embedded in the polymer adjacent or in communication with the microfluidic channel(s).

* * * * *